United States Patent [19]

Hefner, Jr.

[11] Patent Number: 4,540,829
[45] Date of Patent: Sep. 10, 1985

[54] ALLYLATED DI OR POLYCYCLOPENTADIENE DIPHENOLS

[75] Inventor: Robert E. Hefner, Jr., Lake Jackson, Tex.

[73] Assignee: The Dow Chemical Company, Midland, Mich.

[21] Appl. No.: 621,762

[22] Filed: Jun. 18, 1984

Related U.S. Application Data

[63] Continuation-in-part of Ser. No. 446,090, Dec. 2, 1982, abandoned.

[51] Int. Cl.$^3$ ............... C07C 43/205; C07C 43/21; C07C 39/15
[52] U.S. Cl. ............................. 568/634; 568/633; 568/719; 568/632; 252/182; 525/426; 528/183; 528/190
[58] Field of Search ............... 568/633, 634, 719, 632

[56] References Cited

U.S. PATENT DOCUMENTS

| | | | |
|---|---|---|---|
| 3,179,623 | 4/1965 | Bowen | 260/47 |
| 3,256,226 | 6/1966 | Fekete et al. | 260/23.5 |
| 3,301,743 | 1/1967 | Fekete et al. | 161/194 |
| 3,347,935 | 10/1967 | Kaupp et al. | 260/619 |
| 3,367,992 | 2/1968 | Bearden | 260/837 |
| 3,419,624 | 12/1968 | Cotter et al. | 260/619 |
| 3,461,097 | 8/1969 | Cotter et al. | 260/47 |
| 3,539,646 | 11/1970 | Dannels et al. | 568/633 |
| 4,029,848 | 6/1977 | Nelson | 428/430 |
| 4,148,765 | 4/1979 | Nelson | 260/22 |
| 4,167,542 | 9/1979 | Nelson | 525/445 |
| 4,189,548 | 2/1980 | Sakashita et al. | 525/109 |
| 4,233,432 | 11/1980 | Curtis, Jr. | 528/298 |
| 4,246,367 | 1/1981 | Curtis, Jr. | 525/49 |

*Primary Examiner*—Bernard Helfin
*Attorney, Agent, or Firm*—J. G. Carter

[57] ABSTRACT

New compositions of matter are disclosed which are allylated di and polycyclopentadiene diphenols. These new compositions are useful in thermoset resin compositions comprising styrene, a dicyclopentadiene-modified unsaturated polyesteramide and said allylated di and polycyclopentadiene diphenol(s).

13 Claims, No Drawings

ALLYLATED DI OR POLYCYCLOPENTADIENE DIPHENOLS

CROSS REFERENCE TO RELATED APPLICATION

This application is a continuation-in-part of copending application Ser. No. 446,090 filed Dec. 2, 1982 and now abandoned.

BACKGROUND OF THE INVENTION

The present invention pertains to new compositions of matter and to novel thermosettable compositions containing them.

Thermosettable compositions such as unsaturated polyester resins, dicyclopentadiene modified unsaturated polyester resins, unsaturated polyesteramide resins, dicyclopentadiene modified unsaturated polyesteramide resins, vinyl ester resins and the like are well known. Such resins can be employed as is, but are usually diluted with a polymerizable unsaturated monomer such as styrene. These resins are useful in the preparation of castings, laminates, coatings, and the like. However, such resins create relatively large exotherms upon curing, usually with peroxide curing agents, which can induce cracking or fracturing of the cured part, as well as excessive volatile monomer loss.

The present invention provides a thermosettable resin composition which has reduced exotherm temperatures without an unacceptable low reactivity rate and in many instances, the cured resin has an improvement in one or more properties such as heat distortion temperature, hardness, tensile strength, elongation, resistance to thermal aging and the like.

SUMMARY OF THE INVENTION

The present invention is directed to new compositions of matter represented by the formulas

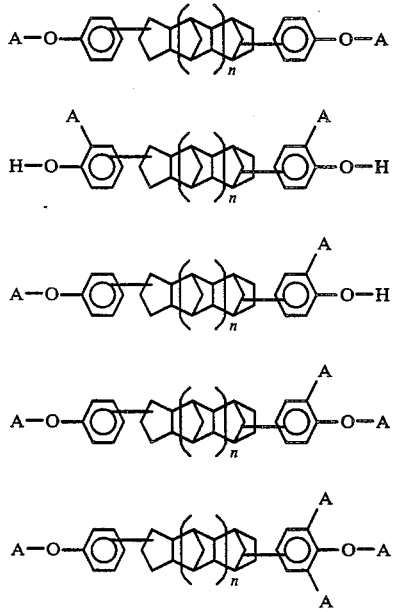

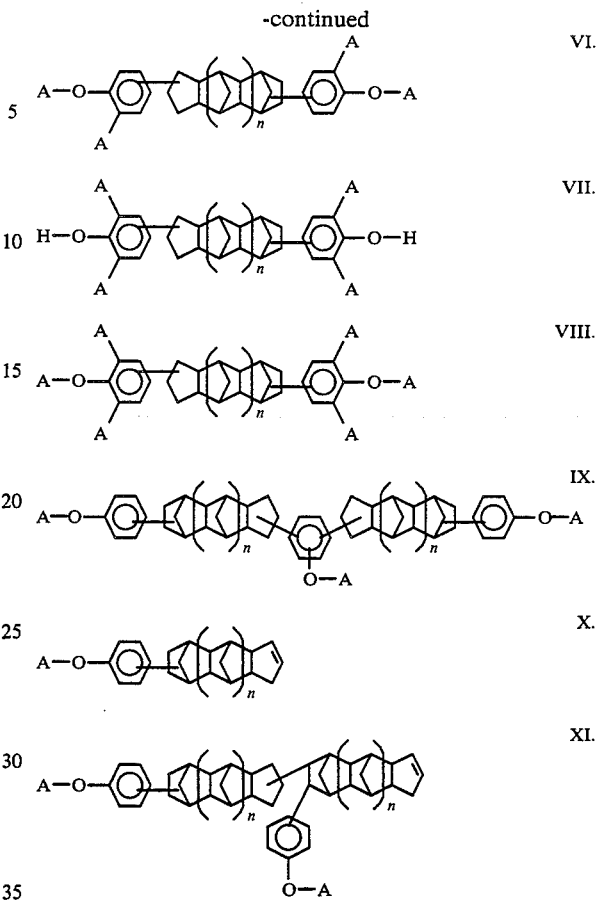

wherein each A is independently a group represented by the formulas

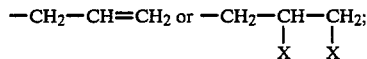

each X is a halogen, preferably chlorine or bromine and each n independently has an average value from zero to about 20, preferably from zero to about 8.

All of the compositions represented by Formulas I, II, III, IV, V, VI, VII, and VIII are isomeric mixtures wherein the substitution of the phenolic groups by dicyclopentadiene is in the ortho and para positions. In compositions represented by Formulas II, III, IV, V, VI, VII, and VIII thermally induced Claisen rearrangement has occurred and the allyl group(s) on the aromatic ring are thus ortho or para to the ether-linked allyl group(s) and/or the free phenolic hydroxyl group(s).

Minor amounts (5 to 6%) of allylated monophenols, isomeric triphenols, and bis(dicyclopentadienyl)diphenols are also present in these compositions and are represented by Formulas IX, X, and XI. It is to be understood that under conditions of thermally induced Claisen rearrangement, the allyl ether group(s) in Formulas IX, X and XI migrate to provide allyl group(s) on the aromatic ring which are ortho or para to the free phenolic hydroxyl group(s) (or ether-linked allyl group(s) if additional allylation reaction is performed). These are present in direct proportion to the amount of each respective non-allylated phenolic that was present as a part of the original dicyclopentadiene diphenol reactant.

The present invention also concerns a composition which is thermosettable upon curing with a curing quantity of a suitable curing agent, which thermosettable composition comprises,
(1) from 5 to about 95, preferably from about 20 to about 80, most preferably from about 45 to about 70, percent by weight (pbw) of at least one resin composition selected from the group consisting of
   (a) unsaturated polyester resins,
   (b) unsaturated polyesteramide resins,
   (c) dicyclopentadiene modified unsaturated polyester resins,
   (d) dicyclopentadiene modified unsaturated polyesteramide resins, and
   (e) vinyl ester resins,
(2) from zero to about 95, preferably from about 70 to about 20, most preferably from about 30 to about 55, pbw of at least one polymerizable ethylenically unsaturated monomer; and
(3) from about 1 to about 50, preferably from about 1 to about 30, most preferably from about 3 to about 15 pbw of a composition represented by the aforementioned formulas I through XI.

DETAILED DESCRIPTION OF THE INVENTION

The allylated dicyclopentadiene or polycyclopentadiene diphenols can be prepared by the transcarbonation process wherein allylmethyl carbonate or a crude mixture containing allylmethyl carbonate is reacted with the dicyclopentadiene diphenol(s) in the presence of a catalytic amount of palladium on carbon and triphenylphosphine. Although less preferred, the allylated dicyclopentadiene diphenols can be prepared by the direct allylation of the dicyclopentadiene diphenol(s) with an allyl halide such as allyl chloride in the presence of an alkaline agent such as an aqueous solution of alkali metal hydroxide. Preferred alkali metal hydroxides include sodium hydroxide and potassium hydroxide. Reaction temperatures of from about 25° to about 150° C. are operable with temperatures of 50° to 100° C. being preferred. If desired, inert solvents such as 1,4-dioxane and phase transfer catalysts such as benzyltrialkylammonium halides or tetraalkylammonium halides can be employed.

The compositions wherein A is

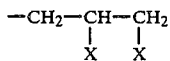

can be prepared by halogenation of the compositions wherein A is an allyl group. The halogenation is carried out in a solvent suitable for the allylated dicyclopentadiene or polycyclopentadiene diphenol. One useful solvent is methylene chloride. The solution is maintained at minus 20° C. to 50° C. and preferably minus 10° to 25° C. The solution is sparged with nitrogen, the halogen, preferably bromine, is added dropwise with stirring while maintaining reaction temperature. Less than stoichiometric amounts of halogen can be used to control the amount of halogen as well as the amount of unreacted allyl groups in the product. It is frequently desireable to maintain the reaction mixture for a period of at least about one-half hour after halogen addition is complete. It may be of advantage to add an oxirane compound, such as an epoxide or polyepoxide, as a hydrogen halide scavenger to aid in stabilization of the product. Removal of the solvent, for example, using distillation under reduced pressure, provides the final product.

Useful products are prepared wherein all or a part of the allyl groups are halogenated. Said products are useful as reactive additives for fire retardant polymers. If all of the allyl groups are completely halogenated, these halogenated products become useful as a non-reactive (no polymerizable allyl groups) additive for fire retardant polymers.

Polycyclopentadiene can be prepared by heating cyclopentadiene at temperatures above 100° C. as disclosed by Kirk-Othmer, ENCYCLOPEDIA OF CHEMICAL TECHNOLOGY, Third Edition, Vol. 7, pp. 417–419 (1979), which is incorporated herein by reference.

The dicyclopentadiene or polycyclopentadiene diphenol starting materials which are allylated to prepare the compositions of the present invention can be prepared by methods taught in U.S. Pat. No. 3,419,624 which is incorporated herein by reference. In a more preferred preparation, phenol is added to a reactor and maintained at 45° C. with stirring under a nitrogen atmosphere. An acidic catalyst, such as Filtrol 1 (an acidified clay manufactured by Filtrol Corporation) is added to the reactor. Dicyclopentadiene (DCPD) is added over a 2.5 to 3.0 hour (9000 to 10,800 s) period so that the reaction temperature reaches 80° C. by the end of the DCPD addition. A molar ratio of phenol to DCPD of about 10 to 1 is preferred while a molar ratio of 20 to 1 is most preferred. The reaction temperature is increased to 150° C. until completion of the reaction, typically about 3.0 hours (10,800 s). The progress of the reaction can be monitored by flame ionization gas chromatography. The reactor is cooled to 60° C. and the catalyst is removed by filtration. The filtrate is vacuum distilled reaching a maximum pot temperature of 240° C. at 20 to 0.5 mm Hg. This removes excess phenol and any dicyclopentadienyl monophenols. The dicyclopentadiene diphenol is removed in 80% yield as a transparent yellow to orange-colored solid. This product contains about 5% higher molecular weight components as determined by gel permeation chromatography. By way of contrast, dicyclopentadiene diphenol prepared using the teachings of U.S. Pat. No. 3,419,624 (i.e., using an acid ion exchange resin catalyst) is of a dark color with cloudiness and contains over 10% higher molecular weight components. Polydicyclopentadiene diphenol is obtained by substituting polydicyclopentadiene for dicyclopentadiene in this preparation.

The norbornyl (dicyclopentadiene) modified unsaturated polyesteramides used herein can be prepared by the methods described herein and they are further described in patent application Ser. No. 333,221, filed. Dec. 21, 1981.

The norbornyl modified unsaturated polyesters used herein can be prepared by the methods described in U.S. Pat. Nos. 4,189,548 or 4,167,542 and 4,148,765.

The unsaturated polyester resins suitable for use herein are well known and are described in Kirk-Othmer Encyclopedia of Chemical Technology, 3rd edition, pp. 575–594 which is incorporated herein by reference.

The unsaturated polyesteramide resins suitable for use herein are prepared by substitution of a portion of the polyol used in the unsaturated polyester resin preparation with a suitable polyamine or mixture of polyamines.

The polyols used in either unsaturated polyesters or unsaturated polyesteramides are from the class of those having the formula: HO—R—OH where R is a divalent organic radical selected from the group consisting of alkylene, ether-linked alkylene, ether-linked arylene, cycloalkylene, polycycloalkylene, bis(alkyl)cycloalkylene, bis(alkyl)polycycloalkylene, and arylene. Mixtures of two or more of such polyols can also be used.

The polyamines used to make unsaturated polyesteramides are from the class of those having the formula:

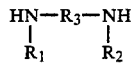

wherein $R_1$ and $R_2$ are independently selected from the group consisting of hydrogen, aliphatic, cycloaliphatic and aromatic radicals, or $R_1$ and $R_2$ taken together with the remainder of the molecule form an aliphatic ring; and $R_3$ is a divalent organic radical selected from the group consisting of alkylene, ether-linked alkylene, ether-linked arylene, alkylene amino-linked alkylene, alkylene amino-linked cycloalkylene, cycloalkylene, polycycloalkylene, arylene, alkylarylene, bis(alkyl)cycloalkylene and bis(alkyl)polycycloalkylene. Mixtures of two or more of such polyamines can also be used.

Typical diamines that are useful are ethylene diamine, propylene diamine, hexane-1,6-diamine, piperazine, 4,4'-methylenebis(cyclohexylamine), 2,2'-bis(4-aminocyclohexyl)propane, 4,4'-diaminodiphenyl ether, bis(aminomethyl)norbornane, toluene diamine, bis-(aminomethyl)-dicyclopentadiene and homopiperazine. Typical polyamines are aminoethylpiperazine and diethylenetriamine.

Representative of the useful diols are: ethylene glycol, propylene glycol, diethylene glycol, dipropylene glycol, dicyclopentadiene dimethanol, bis(hydroxymethyl)norbornane, methyl cyclohexanedimethanol, bis(-hydroxypropyl)bisphenol A and other hydroxyalkylated bisphenols. Typical polyols are pentaerythritol and glycerine propoxylates.

The $\alpha,\beta$-unsaturated polycarboxylic acid is preferably maleic acid, fumaric acid, the anhydride of maleic acid or mixtures of these compounds. Such acids are readily available, have good reactivity with the diol and/or the diamine, and result in products of good properties. Other less preferred unsaturated polycarboxylic acids include itaconic acid, citraconic acid, and the like.

Part of the $\alpha,\beta$-unsaturated polycarboxylic acid may be replaced with a saturated or aromatic polycarboxylic acid to vary the crosslinking potential and physical properties of the unsaturated polyester or polyesteramide. Such acids include the aliphatic acids such as adipic acid and the aromatic acids such as isophthalic acid. Replacement of part of the $\alpha,\beta$-unsaturated acid with such acids is commonplace in the polyester art. Suitable selection of the acid and the amount necessary to achieve a desired purpose will be known to the skilled worker and can be optimized with simple preliminary experiments.

The total amount of acid varies as a function of the total polyol or mixture of polyol and polyamine and, optionally, norbornyl ingredients used.

The terminal group used to modify the unsaturated polyester or polyesteramide is a norbornyl radical. Dicyclopentadiene (DCPD) or dicyclopentadiene concentrates are most preferred norbornyl functional materials to be employed in terminating one or both ends of the chain. Polycyclopentadiene (i.e., DCPD oligomers) or dicyclopentadiene monoalcohol are also preferred species.

DCPD is sold commercially as a product of about 97 or greater percent purity. It is also sold as a $C_{10}$ hydrocarbon concentrate prepared by dimerizing a crude $C_5$ stream from the cracking of hydrocarbons as taught in U.S. Pat. No. 3,557,239.

Examples of some of the dimers which have been identified in these concentrates are the Diels-Alder adducts of two moles of isoprene (isoprene dimers), the adduct of cyclopentadiene and isoprene, the adduct of cyclopentadiene and piperylene and the like.

Either the dicyclopentadiene concentrate or the relatively pure DCPD may be employed in preparing the modified polyesters or polyesteramides.

The modified unsaturated polyesters or polyesteramides can be prepared by a variety of techniques. In a preferred method, molten $\alpha,\beta$-unsaturated carboxylic anhydride is partially hydrolyzed with less than the stoichiometric equivalent of water and reacted with the norbornyl derivative to form esters of that derivative and containing unesterified acid and anhydride. This reaction may conveniently be performed in stages whereby a reactant is added stepwise to control reaction exotherms. The product mixture is then reacted with the polyol and polyamine or the polyol alone to result in the desired modified unsaturated polyester or polyesteramide.

In a typical procedure, molten maleic anhydride and a fraction of the stoichiometric equivalent of water is maintained at an elevated temperature of from about 60° to 130° C. The initial fractional equivalent of dicyclopentadiene (DCPD) is then added and allowed to react. A second fractional equivalent of water and of DCPD is added and allowed to react. Additional fractional equivalents of DCPD are added and each allowed to react before addition of the next increment until the desired amount of DCPD has been added. The number of fractional equivalents can be increased and the size of each fractional equivalent correspondingly decreased to any desired number of fractional equivalents, including continuous addition. The relative size of the fractional equivalents can vary.

The amount of maleic (or other) anhydride employed in this first esterification step may be equal to the equivalent of DCPD in which event the product is essentially all ester. Alternatively, the amount of anhydride may be the equivalent needed to make the ester plus that excess that is to be used in the subsequent esterification or esteramidation step.

To the mixture of esterified DCPD and acid and/or anhydride is added the polyol and polyamine or the polyol alone. After addition of the polyol and polyamine or the polyol alone is complete, the reaction can be driven to maximum yield by maintaining or increasing the temperature until the desired acid number has been reached. Typically, acid numbers of 15 to 35 are preferred, with acid numbers of 15 to 25 being most preferred; although acid numbers that are higher or lower may be tolerated, and, in some instances, may be desired.

In an equally preferred method, molten $\alpha,\beta$-unsaturated carboxylic anhydride is essentially totally hydrolyzed with a stoichiometric or greater equivalent of water and reacted with the norbornyl derivative to form esters of that derivative and containing unesterified acid. This reaction may conveniently be performed in stages whereby a reactant is added stepwise, controlling reaction exotherms. The product mixture is then reacted with the polyol and polyamine or the polyol alone to result in the desired modified unsaturated polyester or polyesteramide.

In a typical procedure, molten maleic anhydride and the stoichiometric or greater equivalent of water are maintained at an elevated temperature from about 50° to 150° C. The temperature is allowed to stabilize at about 120° to 125° C. and the initial fractional equivalent of DCPD is then added and allowed to react. A second fractional equivalent of DCPD is added and allowed to react. Additional fractional equivalents of DCPD are added and each allowed to react before addition of the next increment until the desired amount of DCPD has been added.

The amount of maleic (or other) anhydride employed in this first esterification step may be equal to the equivalent of DCPD in which event the product is essentially all ester. Alternatively, the amount of anhydride may be the equivalent needed to make the ester plus that excess that is to be used in the subsequent esterification or esteramidation step.

The polyol and polyamine or the polyol alone are added to the mixture of esterified DCPD and acid as previously described.

Many other alternate methods will be recognized by the skilled worker. For example, molten maleic anhydride may be added to a mixture of DCPD and water in a reactor. The polyol and polyamine or the polyol alone are added to the mixture of esterified DCPD and acid and/or anhydride as before. Finally, although less preferred, DCPD, maleic anhydride, water and the polyol and polyamine or polyol alone may be simultaneously reacted.

The vinyl ester resins (VER) useful herein are a well known class of resins made from unsaturated carboxylic acids and polyepoxides. Vinyl ester resins are the reaction product of about equivalent amounts of a monounsaturated monocarboxylic acid and a polyepoxide. One class of VER is described in U.S. Pat. No. 3,367,992 where dicarboxylic acid half esters of hydroxyalkyl acrylates or methacrylates are reacted with polyepoxide resins. Bowen in U.S. Pat. Nos. 3,066,122 and 3,179,623 describes the preparation of VER from monocarboxylic acids such as acrylic and methacrylic acid. Bowen also describes alternate methods of preparation wherein a glycidyl methacrylate or acrylate is reacted with the sodium salt of a dihydric phenol such as bisphenol A. VER based on epoxy novolac resins are desribed in U.S. Pat. No. 3,301,743 to Fekete, et al. Fekete, et al describe VER where the molecular weight of the polyepoxide is increased by reacting a dicarboxylic acid with the polyepoxide resin as well as acrylic acid, etc. in U.S. Pat. No. 3,256,226. Other difunctional compounds containing a group which is reactive with an epoxide group, such as an amine, mercaptan, and the like, may be utilized in place of the dicarboxylic acid. All of the above-described resins, which contain the characteristic linkage

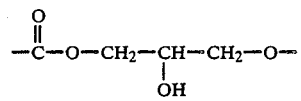

and terminal polymerizable vinylidene groups are classified as VER and are incorporated by reference.

Briefly, any of the known polyepoxides may be employed in the preparation of the vinyl ester resins. Useful polyepoxides are glycidyl polyethers of both polyhydric alcohols and polyhydric phenols, such as the diglycidyl ether of bisphenol A, epoxy novolacs, epoxidized fatty acids or drying oil acids, epoxidized diolefins, epoxidized di-unsaturated acid esters as well as epoxidized unsaturated polyester, so long as they contain more than one oxirane group per molecule. The polyepoxides may be monomeric or polymeric.

Preferred polyepoxides are glycidyl polyethers of polyhydric alcohol or phenols having weights per epoxide group of about 150 to 2000. The polyepoxides may be nuclearly substituted with halogen, preferably bromine. These polyepoxides are usually made by reacting at least about two moles of an epihalohydrin or glycerol dihalohydrin with one mole of the polyhydric alcohol or polyhydric phenol and a sufficient amount of a caustic alkali to combine with the halogen of the halohydrin. The products are characterized by the presence of more than one epoxide group per molecule, i.e., a 1,2-epoxy equivalency greater than one.

Vinyl ester resins are commercially available from the Dow Chemical Company under the trademark DERAKANE.

Any polymerizable ethylenically unsaturated monomer can be used herein. Such monomers include both monovinyl and polyvinyl monomers. Typical monomers include the alkenyl aromatic monomers such as styrene, α-methylstyrene, chlorostyrene, divinylbenzene, vinyltoluene, t-butylstyrene, and the like; and alkyl and hydroxyalkyl esters of acrylic and methacrylic acid such as the methyl, ethyl, propyl, butyl, cyclohexyl, and hydroxyethyl esters. In addition to the above, other monomers that are especially useful for ultraviolet light curable systems such as 2-acetoxyalkyl acrylates, pentaerythritol di-, tri-, or tetra-acrylate may be used.

Suitable curing agents which can be employed to cure the compositions of the present invention include, for example, free radical forming catalysts. Examples of these catalysts are benzoyl peroxide, tertiary butyl peroxide, methylethyl ketone peroxide, and the like. It is frequently of value to add accelerators such as cobalt naphthenate, dimethylaniline, and the like.

The compositions of the present invention are useful in the preparation of castings, laminates, coatings and the like.

The following examples are illustrative of the invention but are not to be construed as to limiting the scope thereof in any manner.

EXAMPLE 1

A transcarbonation reaction was used to prepare the bis(allylether) of dicyclopentadiene diphenol, as follows:

Allyl alcohol (48.7 grams, 0.84 mole), dimethyl carbonate (75.6 grams, 0.84 mole), and sodium methoxide catalyst (0.10 gram) were added to a reactor and maintained at room temperature (25° C.) with stirring under a nitrogen atmosphere. An equilibrium mixture of allylmethyl carbonate, diallyl carbonate, and methanol was rapidly formed. After thirty minutes (1800 s), dicyclopentadiene diphenol (24.7 grams, 0.0771 mole), triphenylphosphine (0.60 gram) and 5.0% palladium or carbon (0.20 gram) were added to the reactor and heating was started. The dicyclopentadiene diphenol used was a distilled product containing in excess of 95% isomeric dicyclopentadiene diphenols, less than 1% dicyclopentadiene monophenols, with the remainder being isomeric triphenols and bis(dicyclopentadienyl)diphenols. The dicyclopentadiene diphenols were approximately 50% ortho and 50% para isomers. The reaction mixture was maintained for four hours (14,400 s) at 82° C. and then cooled to room temperature. Filtration through Celite, followed by vacuum stripping at 100° C. and 10 mm provided a pale-yellow oil (31.3 grams 100% yield). Nuclear magnetic resonance spectroscopy confirmed the product as the bis(allylether) of dicyclopentadiene diphenol. Gas chromatographic-mass spectroscopic analysis confirmed the presence of about 95% bis(allylether) of dicyclopentadiene diphenol (Formula I, n=0, A=—$CH_2$—CH=$CH_2$), about 1% monoallylether of dicyclopentadiene monophenol (Formula X, n=0, A=—$CH_2$—CH=$CH_2$), and about 4% of tris(allylether) of dicyclopentadiene triphenol (Formula IX, n=0, A=—$CH_2$—CH=$CH_2$) and bis(allylether) of bis(dicyclopentadienyl)diphenol (Formula XI, n=0, A=—$CH_2$—CH=$CH_2$) combined.

EXAMPLE 2

A phase transfer catalyzed direct allylation reaction was used to prepare the bis(allylether) of dicyclopentadiene diphenol, as follows:

Dicyclopentadiene diphenol (64.1 grams, 0.20 mole), p-dioxane (200 milliliters), water (200 milliliters), sodium hydroxide (16.4 grams, 0.41 mole), and 60% aqueous benzyltrimethylammonium chloride catalyst (6.2 grams, 0.02 mole) were added to a reactor with stirring under a nitrogen atmosphere. The dicyclopentadiene diphenol was of the same composition as that employed in Example 1. The reactor was heated to 85° C. and then allyl chloride (76.5 grams, 1.0 mole) was added dropwise over six hours (21,600 s). The reactor was cooled to 77° C. and maintained at this temperature for fourteen hours (50,400 s). After cooling to room temperature (25° C.), the reaction mixture was neutralized with dilute hydrochloric acid, then multiply extracted with toluene. Vacuum stripping to remove the toluene solvent provided a pale-yellow oil (78.0 grams, 96.9% yield). Nuclear magnetic resonance spectroscopy confirmed the product as the bis(allylether) of dicyclopentadiene diphenol containing less than about 5% of the Claisen rearrangement products of the bis(allylether) of dicyclopentadiene diphenol (Formula II, n=0, A=—$CH_2$—CH=$CH_2$ and Formula III, n=0, A=—$CH_2$—CH=$CH_2$). Gas chromatographic-mass spectroscopic analysis confirmed the presence of about 90% bis(allylether) of dicyclopentadiene diphenol (Formula I, n=0, A=—$CH_2$—CH=$CH_2$), about 5% of disallylated dicyclopentadiene diphenols and trisallylated dicyclopentadiene diphenol (Formula II, n=0, A=—$CH_2$—CH=$CH_2$; Formula III, n=0, A=—$CH_2$—CH=$CH_2$; Formula IV, n=0, A=—$CH_2$—CH=$CH_2$) combined, about 1% monoallylether of dicyclopentadiene monophenol (Formula X, n=0, A=—$CH_2$—CH=$CH_2$) and about 4% of tris(allylether) of dicyclopentadiene triphenol (Formula IX, n=0, A=—$CH_2$—CH=$CH_2$) and bis(allylether) of bis(dicyclopentadienyl)diphenol (Formula XI, n=0, A=—$CH_2$—CH=$CH_2$) combined. Traces of the Claisen rearrangement products of the monoallylether of dicyclopentadiene monophenol, the tris(allylether) of dicyclopentadiene triphenol and the bis(allylether) of bis(dicyclopentadienyl)diphenol were also present.

EXAMPLE 3

A dicyclopentadiene modified unsaturated polyesteramide alkyd was prepared for formulation with styrene and the bis(allylether) of dicyclopentadiene diphenol from Example 1:

Maleic anhydride (686.42 grams, 7.00 moles) was added to a reactor and heated to a clear, stirred solution maintained at 100° C. under a nitrogen atmosphere. Water (127.94 grams, 7.10 moles) was added inducing a maximum exotherm of 135° C. one minute (60 s) later. Fifteen minutes (900 s) the reactor after the initial water addition was air-cooled to 121° C. and dicyclopentadiene (277.64 grams, 2.10 moles) was added. A maximum exotherm of 125° C. resulted two minutes (120 s) later and after an additional three minutes (180 s), air cooling reduced the reaction temperature to 120° C. Fifteen minutes (900 s) after the initial dicyclopentadiene addition, a second aliquot of dicyclopentadiene (277.64 grams, 2.10 moles) was added. A maximum exotherm of 124° C. resulted five minutes (300 s) later and after an additional five minutes (300 s), air cooling reduced the reaction temperature to 120° C. A final aliquot of dicyclopentadiene (277.64 grams, 2.10 moles) was added fifteen minutes (900 s) after the second dicyclopentadiene addition and the 120° C. reaction temperature was re-achieved three minutes (180 s) later. Thirty minutes (1800 s) later, propylene glycol (287.66 grams, 3.78 moles) and piperazine (36.18 grams, 0.420 mole) were added and nitrogen sparging was increased to four liters per minute, the steam condenser was started, and the temperature controller was set at 160° C. This temperature was achieved thirty-two minutes (1920 s) later. After two hours (7200 s), the temperature controller was set at 205° C. and this temperature was achieved twenty-five minutes (1500 s) later. After fourteen hours (50,400 s), 151.5 milliliters of water layer and 32 milliliters of organic material were recovered into the Dean Stark trap. The reactor was cooled to 168° C. and 100 ppm of hydroquinone was added. The modified polyesteramide alkyd was recovered as a clear, light-yellow colored solid with a final acid number of 18.8.

A portion of the modified unsaturated polyesteramide (199.5 grams), styrene (115.5 grams), and the bis(allylether) of dicyclopentadiene diphenol (35.0 grams) from Example 1 were formulated to provide a 57.0, 33.0, 10.0% solution, respectively. This solution was used to determine the Brookfield viscosity (25° C.), SPI (84° C.) gel and cure times plus maximum exotherm, and a clear, unfilled casting was prepared for use in mechanical property evaluations. A cure system of 1.0% benzoyl peroxide and 0.01% dimethylaniline was used at room temperature (25° C.), followed by post-curing for two hours (7200 s) at 200° F. (93° C.). Tensile test pieces (eight) and flexural test pieces (six) were prepared from the clear, unfilled casting and tested using an Instron machine with standard methods (ASTM D-638 and D-790). A pair of heat distortion temperature test pieces were prepared from the clear, unfilled casting and tested using an Aminco Plastic Deflection Tester (American Instrument Co.) with standard methods (ASTM D-648). All Barcol hardness values are on the 934-1 scale. The results are reported in Table I.

EXAMPLE 4

A portion of the modified unsaturated polyesteramide (199.5 grams) from Example 3, styrene (133.0 grams), and the bis(allylether) of dicyclopentadiene diphenol (17.5 grams) from Example 2 were formulated to provide a 57.0, 38.0, 5.0% solution, respectively. The physical and mechanical properties were evaluated using the method of Example 3. The results are reported in Table I.

Comparative Experiment A

A portion of the modified polyesteramide (199.5 grams) from Example 3 and styrene (150.5 grams) were formulated to provide a 57.0, 43.0% solution, respectively. The physical and mechanical properties were evaluated using the method of Example 3. The results are reported in Table I.

TABLE I

|  |  | Ex. 3 | Ex. 4 | Comp. Expt. A |
|---|---|---|---|---|
| Brookfield Viscosity (cp) |  | 811 | 531 | 241 |
| SPI Gel Test |  |  |  |  |
| Gel time, min/sec |  | 6.0/360 | 3.6/216 | 3.3/198 |
| Cure time, min/sec |  | 9.4/564 | 5.7/342 | 5.2/312 |
| Maximum exotherm (°C.) |  | 153 | 200 | 216 |
| Average Barcol Hardness |  | 19 | 43 | 43 |
| Heat Distortion Temperature, °F./°C. |  | 163/72.8 | 209/98.3 | 231/110.6 |
| Tensile Strength, | psi | 5,900 | 5,800 | 4,300 |
|  | kPa | 40,700 | 40,000 | 29,600 |
| Elongation (%) |  | 2.7 | 1.5 | 1.0 |
| Flexural Strength, | psi | 10,200 | 13,800 | 11,600 |
|  | kPa | 70,300 | 95,100 | 80,000 |
| Flexural Modulus, | psi | 260,000 | 560,000 | 550,000 |
|  | kPa | 1,800,000 | 3,860,000 | 3,800,000 |

EXAMPLE 5

A bisallylated dicyclopentadiene diphenol wherein the allyl groups were located solely on the aromatic rings was prepared as follows:

The transcarbonation reaction of Example 1 was scaled up fourfold and repeated to provide the bis(allylether) of dicyclopentadiene diphenol. The bis(allylether) of dicyclopentadiene diphenol was then added to a reactor and maintained with stirring under a nitrogen atmosphere and heating was started. The reaction was maintained for 1 hour (3600 s) at 200° C. then cooled to 100° C. and the product recovered while still fluid. The product was recovered as a clear, light amber-colored solid in quantitative yield. Nuclear magnetic resonance spectroscopy confirmed the product as bisallylated dicyclopentadiene diphenol wherein the allyl groups were both located solely on the aromatic rings. (Formula II, n=0, A=—$CH_2$—CH=$CH_2$). Gas chromatographic-mass spectroscopic analysis demonstrated that the minor components (Formulas IX, X and XI all where n=0, A=—$CH_2$—CH=$CH_2$) were present in the proportions indicated by Example 1, however, they were converted to the corresponding isomeric allylated phenols during the thermally induced Claisen rearrangement.

EXAMPLE 6

A portion of the bisallylated dicyclopentadiene diphenol of Example 5 was converted to a tetraallylated dicyclopentadiene diphenol as follows:

Allyl alcohol (71.92 grams, 1.24 moles), dimethyl carbonate (111.6 grams, 1.24 moles), and sodium methoxide catalyst (0.15 gram) were added to a reactor and maintained at room temperature (25° C.) with stirring under a nitrogen atmosphere. An equilibrium mixture of allylmethyl carbonate, diallyl carbonate, and methanol was rapidly formed. After thirty minutes (1800 s), bisallylated dicyclopentadiene diphenol (50.0 grams, 0.124 mole) from Example 5, triphenylphosphine (0.477 gram), and 5.0% palladium on carbon (0.32 gram) were added to the reactor and heating was started. The reaction mixture was maintained for four hours (14,400 s) at 80° C. and then cooled to room temperature (25° C.). Filtration through Celite, followed by vacuum stripping at 100° C. and 10 mm provided a clear, yellow-colored oil (59.85 grams, 99.6% yield). Nuclear magnetic resonance spectroscopy confirmed the product as the tetraallylated dicyclopentadiene diphenol wherein two of the allyl groups were present as ether-linked substituents and two of the allyl groups were present as substituents on the aromatic rings (Formula VI, n=0, A=—$CH_2$—CH=$CH_2$).

EXAMPLE 7

An orthophthalate unsaturated polyester alkyd was prepared for formulation with styrene and the tetraallylated dicyclopentadiene diphenol from Example 6:

Maleic anhydride (176.51 grams, 1.80 moles) and phthaic anhydride (177.74 grams, 1.20 moles) were added to a reactor and heated to a white, stirred slurry maintained at 100° C. under a nitrogen atmosphere. Propylene glycol (251.13 grams, 3.30 moles) was added and a maximum exotherm of 135° C. occurred twenty-five minutes (1500 s) later. At this time, nitrogen sparging was increased to one liter per minute, the steam condenser was started, and the temperature controller was set at 160° C. This temperature was achieved seven minutes (420 s) later. After two hours (7200 s), the temperature controller was set at 205° C. and this temperature was achieved nineteen minutes (1140 s) later. After four hours (14,400 s), 56 milliliters of water layer was recovered into the Dean Stark trap. The reactor was cooled to 168° C. and 100 ppm of hydroquinone was added. The unsaturated polyester alkyd was recovered as a transparent solid with a final acid number of 32.4.

A portion of the unsaturated polyester (199.5 grams), styrene (133.0 grams), and the tetraallylated dicyclopentadiene diphenol (17.5 grams) from Example 6 were formulated to provide a 57.0, 38.0, 5.0% solution, respectively. The physical and mechanical properties were evaluated using the method of Example 3. The results are reported in Table II.

Comparative Experiment B

A portion of the unsaturated polyester (199.5 grams) from Example 7 and styrene (150.5 grams) were formulated to provide a 57.0, 43.0% solution, respectively. The physical and mechanical properties were evaluated using the method of Example 3. The results are reported in Table II.

TABLE II

|  |  | Ex. 7 | Comp. Expt. B |
|---|---|---|---|
| Brookfield Viscosity (cp) |  | 282 | 141.5 |
| SPI Gel Test |  |  |  |
| Gel time, min/sec |  | 2.6/156 | 2.4/144 |
| Cure time, min/sec |  | 4.4/264 | 4.0/240 |
| Maximum exotherm (°C.) |  | 194 | 229 |
| Average Barcol Hardness |  | 40 | 46 |
| Heat Distortion Temperature, °F./°C. |  | 172/77.8 | 204/95.6 |
| Tensile Strength, | psi | 8,700 | 8,300 |
|  | kPa | 60,000 | 57,200 |
| Elongation (%) |  | 2.6 | 1.8 |
| Flexural Strength, | psi | 17,500 | 21,100 |
|  | kPa | 120,700 | 145,500 |
| Flexural Modulus, | psi | 530,000 | 610,000 |
|  | kPa | 3,650,000 | 4,210,000 |

EXAMPLE 8

A pair of 5.0 by 0.5 by 0.125 inch (12.7 by 1.27 by 0.318 cm) test pieces were prepared from the clear, unfilled castings of both Example 7 and Comparative Experiment B. The two sets of test pieces were placed on a flat aluminum tray and suspended in a forced air, convection-type oven. An additional curing cycle of three hours (10,800 s) at 94° C., two hours (7200 s) at 125° C., and three hours (10,800 s) at 175° C. was completed. After this additional curing, the initial weight of each test piece was obtained. The test pieces were then placed back in the oven and maintained at 175° C. They were removed and weighed after 15 and 39 hours (54,000 and 140,400 s) of exposure. After the 39 hour (140,400 s) interval, the exposure temperature was increased to 200° C. and the test pieces were removed and weighed after 48 total hours (172,800 s) of exposure. The results are reported in Table III wherein the weight loss is expressed as the percent of the initial weight of each respective test piece.

TABLE III

| Total Hours/Seconds of Thermal Exposure | Percent Weight Loss | | | |
|---|---|---|---|---|
|  | Example 7 | | Comparative Experiment B | |
|  | 1 | 2 | 1 | 2 |
| 15/54,000 | −0.46 | −0.44 | −0.61 | −0.63 |
| 39/140,400 | −0.67 | −0.65 | −1.03 | −1.06 |
| 48/172,800 | −1.76 | −1.72 | −2.89 | −2.89 |

EXAMPLE 9

A series of 5.0 by 0.5 by 0.125 inch (12.7 by 1.27 by 0.318 cm) heat distortion temperature test pieces were prepared from the clear, unfilled castings of both Example 4 and Comparative Experiment A. The test pieces were placed on a flat aluminum tray which was then suspended in a forced-air, convection-type oven. Further curing at 94° C. for three hours (10,800 s) and 125° C. for two hours (7200 s) was completed, followed by heat aging for the indicated times and temperatures summarized in Table IV. Test pieces were removed at the indicated exposure intervals and the heat distortion temperatures were determined using the method of Example 3. The results are reported in Table IV.

TABLE IV

| Total Hours/Sec of Thermal Exposure | Temperature (°C.) | Heat Distortion Temperature (°F./°C.) | |
|---|---|---|---|
|  |  | Example 4 | Comparative Experiment A |
| 3/10,800 | 175 | 260/126.7 | 295/146.1 |
| 15/54,000 | 175 | 286/141.1 | 310/154.4 |
| 39/140,400 | 175 | 295/146.1 | 313/156.1 |
| 75/270,000 | 200 | 324/162.2 | 319/159.4 |
| 138/496,800 | 200 | 329/165.0 | 338/170.0 |
| 154/554,400 | 200 | 340/171.1 | 353/178.3 |
| 178/640,800 | 200 | 350/176.7 | 338/170.0 |

EXAMPLE 10

A portion of the tetraallylated dicyclopentadiene diphenol from Example 6 was partially brominated, as follows:

Tetraallylated dicyclopentadiene diphenol (36.56 grams, 0.0761 mole) from Example 6 and methylene chloride (250 grams) were added to a reactor and maintained under a nitrogen atmosphere with stirring. The reactor was chilled using a methylene chloride-dry ice bath. Bromine (36.47 grams, 0.2282 mole) was added dropwise to the solution over a six-minute (360 s) period during which time the reaction temperature was kept between minus 5° to 10° C. After an additional fifteen minutes (900 s) at the the minus 10° C. reaction temperature, 1.0 percent by weight of the diglycidyl ether of a polyglycol (sold commercially as D.E.R. ®736 epoxy resin) having an epoxy equivalent weight of 175–205 was added as a hydrohalide scavenger then the reactor was allowed to warm to room temperature (25° C.). Vacuum stripping at 75° C. and 10 mm provided an amber-colored solid (58.80 grams), wherein about 1.8 allyl groups per molecule of tetraallylated dicyclopentadiene diphenol were converted to dibromopropane groups. Nuclear magnetic resonance spectroscopy was used to confirm the product structure (Formula VI, n=0, A=(major)

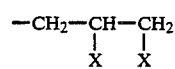

where X=Br and (minor) —CH$_2$—CH=CH$_2$).

EXAMPLE 11

A portion of the dicyclopentadiene modified unsaturated polyesteramide (30.0 grams) of Example 3 was formulated with styrene (30.0 grams) and a portion of the partially brominated tetraallylated dicyclopentadiene diphenol of Example 10 to provide a 40.0, 40.0, 20.0 percent solution, respectively. The formulation was used to prepare a clear, unfilled casting. A cure system of 2.0% benzoyl peroxide and 0.01% dimethylaniline was used at room temperature (25° C.), followed by post-curing for two hours (7200 s) at 200° F. (93° C.). Test pieces were prepared from the clear, unfilled casting and used with standard methods (ASTM D-2863-76) to determine oxygen index. The oxygen index value was 26.75.

EXAMPLE 12

A vinyl ester resin was prepared for formulation with the bis(allylether) of dicyclopentadiene diphenol:

About 1 equivalent of methacrylic acid is reacted with 0.75 equivalent of an epoxy novolac having an epoxide equivalent weight (EEW) of 175–182 and 0.25 equivalent of a glycidyl polyether of bisphenol A having an EEW of 186–192. The above reactants are heated to 115° C. with catalyst and hydroquinone present until the carboxylic acid content reaches about 1 percent. The reactants are cooled and then styrene (containing 50 ppm of t-butyl catechol) is added. The final vinyl ester resin diluted with styrene has a pH of 7.7 and contains approximately:

| Contents | % |
|---|---|
| styrene | 36 |
| methacrylic acid | 20.6 |
| epoxy novolac (EEW = 175–182) | 32.1 |
| diglycidyl ether of bisphenol A (EEW = 186–192) | 11.3 |
| | 100.0 |

A portion of the styrenated vinyl ester resin (300.0 grams) and the bis(allylether) of dicyclopentadiene diphenol (22.58 grams) were formulated to provide a 93.0, 7.0% solution, respectively. The bis(allylether) of dicyclopentadiene diphenol used in this formulation was prepared using the method of Example 1. The physical and mechanical properties of the resin formulation were determined using the method of Example 3. The results are reported in Table V.

Comparative Experiment C

A portion of the styrenated vinyl ester resin of Example 12 was used to determine physical and mechanical properties using the method of Example 3. The results are reported in Table V.

TABLE V

| | | Ex. 12 | Comp. Expt. C |
|---|---|---|---|
| Brookfield Viscosity (cp) | | 295 | 260 |
| SPI Gel Test | | | |
| Gel time, min/sec | | 12.0/720 | 8.0/480 |
| Cure time, min/sec | | 15.8/948 | 9.5/570 |
| Maximum exotherm (°C.) | | 178 | 209 |
| Average Barcol Hardness | | 42 | 39 |
| Heat Distortion Temperature, °F./°C. | | 201/93.9 | 214/101.1 |
| Tensile Strength, | psi | 10,800 | 9,000 |
| | kPa | 74,500 | 62,100 |
| Elongation (%) | | 2.8 | 2.8 |
| Flexural Strength, | psi | 21,700 | 19,200 |
| | kPa | 149,600 | 132,400 |
| Flexural Modulus, | psi | 660,000 | 640,000 |
| | kPa | 4,550,000 | 4,410,000 |

EXAMPLE 13

A mixture of an unsaturated polyester alkyd, a dicyclopentadiene modified unsaturated polyesteramide alkyd and a vinyl ester resin were prepared for formulation with styrene and the bis(allylether) of dicyclopentadiene diphenol.

Tetrahydrophthalic anhydride (456.45 grams, 3.00 moles), maleic anhydride (294.18 grams, 3.00 moles), propylene glycol (251.13 grams, 3.30 moles) and dipropylene glycol (442.79 grams, 3.30 moles) were condensed to provide an unsaturated polyester alkyd with a final acid number of 25.4. A portion of this unsaturated polyester alkyd (25.0 grams), the modified unsaturated polyesteramide (114.0 grams) from Example 3, the styrenated vinyl ester resin (50.0 grams) from Example 12, styrene (86.0 grams) and bis(allylether) of dicyclopentadiene diphenol (18.5 grams) prepared using the method of Example 1 were formulated to provide the following solution:

| | Percent by Weight |
|---|---|
| unsaturated polyester | 8.52 |
| dicyclopentadiene modified unsaturated polyesteramide | 38.84 |
| vinyl ester (active) | 10.90 |
| styrene | 35.44 |
| bis(allylether) of dicyclopentadiene diphenol | 6.30 |

The physical and mechanical properties were evaluated using the method of Example 3. The results are reported in Table VI.

COMPARATIVE EXPERIMENT D

A portion of the unsaturated polyester alkyd (25.0 grams) from Example 13, the modified unsaturated polyesteramide (114.0 grams) from Example 3, the styrenated vinyl ester resin (50.0 grams) from Example 12 and styrene (104.5 grams) were formulated to provide the following solution:

| | Percent by Weight |
|---|---|
| unsaturated polyester | 8.52 |
| dicyclopentadiene modified unsaturated polyesteramide | 38.84 |
| vinyl ester (active) | 10.90 |
| styrene | 41.74 |

The physical and mechanical properties were evaluated using the method of Example 3. The results are reported in Table VI.

TABLE VI

| | | Ex. 13 | Comp. Expt. D |
|---|---|---|---|
| Brookfield Viscosity (cp) | | 208 | 97 |
| SPI Gel Test | | | |
| Gel time, min./sec. | | 11.2/672 | 6.7/402 |
| Cure time, min./sec. | | 15.7/942 | 9.2/552 |
| Maximum exotherm (°C.) | | 160 | 216 |
| Average Barcol Hardness | | 42 | 45 |
| Heat Distortion Temperature, °F./°C. | | 174/79 | 234/112 |
| Tensile Strength, | psi | 8,926 | 7,241 |
| | kPa | 61,543 | 49,925 |
| Elongation (%) | | 2.54 | 1.69 |
| Flexural Strength, | psi | 15,729 | 15,539 |
| | kPa | 108,448 | 107,138 |
| Flexural Modulus, | psi | 500,000 | 574,000 |
| | kPa | 3,447,400 | 3,957,615 |

I claim:
1. A new composition of matter represented by the following Formulas I, II, III, IV, V, VI, VII, VIII, IX, X, and XI

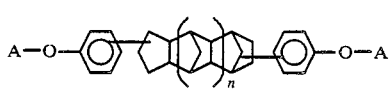

I.

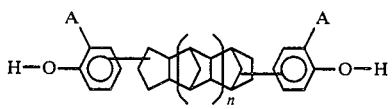

II.

-continued

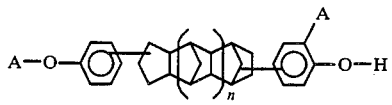
III.

IV.

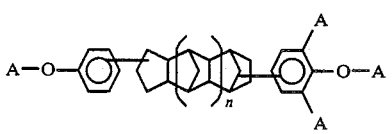
V.

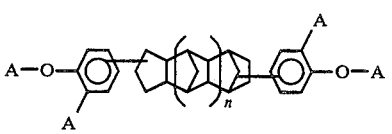
VI.

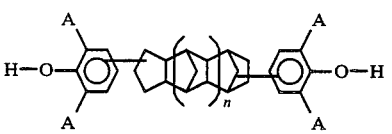
VII.

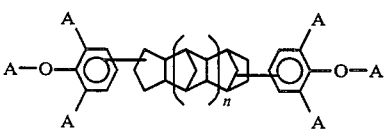
VIII.

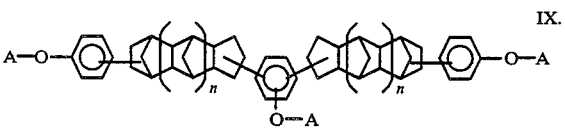
IX.

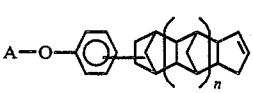
X.

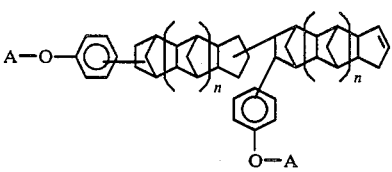
XI.

wherein each A is independently a group represented by the formulas

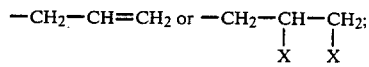

X is a halogen and n has an average value from zero to about 20.

2. A composition of claim 1 wherein at least 90% by weight is represented by Formula I; each A is —CH$_2$—CH=CH$_2$ and n has an average value of from zero to about 8.

3. A composition of claim 2 wherein n has a value of zero.

4. A composition of claim 1 wherein at least 90% by weight is represented by Formula II; each A is —CH$_2$—CH=CH$_2$ and n has an average value of from zero to about 20.

5. A composition of claim 4 wherein n has a value of zero.

6. A composition of claim 1 wherein at least about 90% by weight is represented by Formula VI; each A is —CH$_2$—CH=CH$_2$ and n has an average value of from zero to about 20.

7. A composition of claim 6 wherein n has a value of zero.

8. A composition of claim 1 wherein at least 90% by weight is represented by Formula I; at least 10% of the A groups are $$-CH_2-\underset{X}{CH}-\underset{X}{CH_2};$$

X is chlorine or bromine and n has an average value of from zero to about 20.

9. A composition of claim 8 wherein X is bromine and n is zero.

10. A composition of claim 1 wherein at least 90% by weight is represented by Formula II; at least 10% of the A groups are $$-CH_2-\underset{X}{CH}-\underset{X}{CH_2};$$

X is chlorine or bromine and n has a value from zero to about 20.

11. A composition of claim 10 wherein X is bromine and n is zero.

12. A composition of claim 1 wherein at least 90% by weight is represented by Formula VI wherein at least 10% of the A groups are $$-CH_2-\underset{X}{CH}-\underset{X}{CH_2};$$

X is chlorine or bromine and n has an average value of from zero to about 20.

13. A composition of claim 12 wherein X is bromine and n is zero.

* * * * *